(12) United States Patent
Thompson et al.

(10) Patent No.: US 7,048,934 B2
(45) Date of Patent: May 23, 2006

(54) COMBINED REGULATION OF NEURAL CELL PRODUCTION

(75) Inventors: Bradley G. Thompson, Calgary (CA); Samuel Weiss, Calgary (CA); Tetsuro Shingo, Aoe (JP)

(73) Assignee: Stem Cell Therapeutics Inc., Calgary ( * ) Notice: Subject to any disclaimer, the term of this patent is extended or adjusted under 35 U.S.C. 154(b) by 0 days.

(21) Appl. No.: 10/231,493

(22) Filed: Aug. 30, 2002

(65) Prior Publication Data

US 2003/0049838 A1   Mar. 13, 2003

Related U.S. Application Data

(60) Provisional application No. 60/316,365, filed on Aug. 30, 2001, provisional application No. 60/316,579, filed on Aug. 31, 2001, provisional application No. 60/322,514, filed on Sep. 14, 2001, provisional application No. 60/386,404, filed on Jun. 7, 2002.

(51) Int. Cl.
A61K 38/00 (2006.01)
A61K 38/16 (2006.01)
A61K 38/18 (2006.01)

(52) U.S. Cl. .................. 424/198.1; 435/377; 435/365; 435/368; 530/399; 514/12

(58) Field of Classification Search ............... 514/2, 514/14; 435/368, 375
See application file for complete search history.

(56) References Cited

U.S. PATENT DOCUMENTS

| | | | |
|---|---|---|---|
| 5,023,252 A | 6/1991 | Hseih | |
| 5,128,242 A | 7/1992 | Arimura et al. | |
| 5,198,542 A | 3/1993 | Onda et al. | |
| 5,208,320 A | 5/1993 | Kitada et al. | |
| 5,268,164 A | 12/1993 | Kozarich et al. | |
| 5,326,860 A | 7/1994 | Onda et al. | |
| 5,506,107 A | 4/1996 | Cunningham et al. | |
| 5,506,206 A | 4/1996 | Kozarich et al. | |
| 5,527,527 A | 6/1996 | Friden | |
| 5,547,935 A | 8/1996 | Mullenbach et al. | |
| 5,559,143 A * | 9/1996 | McDonald et al. | 514/419 |
| 5,614,184 A | 3/1997 | Sytkowski et al. | |
| 5,623,050 A | 4/1997 | Kitada et al. | |
| 5,686,416 A | 11/1997 | Kozarich et al. | |
| 5,723,115 A | 3/1998 | Serrero | |
| 5,750,376 A | 5/1998 | Weiss et al. | |
| 5,753,506 A | 5/1998 | Johe | |
| 5,773,569 A | 6/1998 | Wrighton et al. | |
| 5,801,147 A | 9/1998 | Kitada et al. | |
| 5,833,988 A | 11/1998 | Friden | |
| 5,837,460 A | 11/1998 | Von Feldt et al. | |
| 5,851,832 A | 12/1998 | Weiss et al. | |
| 5,877,169 A * | 3/1999 | Simpkins | 514/179 |
| 5,885,574 A | 3/1999 | Elliott | |
| 5,955,346 A | 9/1999 | Wells et al. | |
| 5,977,307 A | 11/1999 | Friden et al. | |
| 5,980,885 A | 11/1999 | Weiss et al. | |
| 6,015,555 A | 1/2000 | Friden | |
| 6,048,971 A | 4/2000 | Sytkowski et al. | |
| 6,191,106 B1 | 2/2001 | Mullenbach et al. | |
| 6,239,105 B1 | 5/2001 | Brewitt | |
| 6,242,563 B1 | 6/2001 | Dong | |
| 6,329,508 B1 | 12/2001 | Friden | |
| 6,333,031 B1 | 12/2001 | Olsson et al. | |
| 6,413,952 B1 | 7/2002 | Luengo et al. | |
| 6,429,186 B1 | 8/2002 | Fuh et al. | |
| 2002/0098178 A1 | 7/2002 | Brand | |

FOREIGN PATENT DOCUMENTS

| | | |
|---|---|---|
| WO | WO 96 40231 | 12/1996 |
| WO | WO 97 48729 | 12/1997 |
| WO | WO 99/15191 A | 4/1999 |
| WO | WO 99/21966 A | 5/1999 |
| WO | WO 00/05260 A | 2/2000 |
| WO | WO 00/13650 A | 3/2000 |

OTHER PUBLICATIONS

Konishi et al. Brain Research. 1993, 609:29-35.*
Gage et al. "Mammalian Neural Stem Cell". Science. Feb. 2000. vol. 287, pp. 1433-1438.*
Cerami et al. Seminars in Oncology, (Apr. 2001), vol. 28, No. 2, Suppl 8, pp. 66-70.*
Kandel et al. "Principles of Neural Science". 1991, p. 981.*
Phelps, C.J. et al., "Pituitary hormones as neurotrophic signals: Update on hypothalamic differentiation in genetic models of altered feedback", *Proceedings of the Society for Experimental Biology and Medicine*, 222(1):39-58 (1999).
Phelps, C.J, et al., "Stimulatory effect of human, but not bovie, growth hormone expression on numbers of tuberoinfundibular dopaminergic neurons in transgenic mice", *Endocrinology*, 138(7):2849-2855 (1997).
Sorokan, et al., "Erythropoietin mediates increased neurogenesis by embryonic CNS stem cells following a modest hypoxic insult", *Society for Neuroscience Abstracts*, 23(1/2):320 (1997).
Dicco-Bloom et al., "The PACAP Ligand/Receptor System Regulates Cerebral Cortical Neurogenesis", Annals of the New York Academy of Sciences, pp. 274-289 (1998).
Lee et al., "Pituitary Adenylyl Cyclase-Activating Polypeptide Stimulates DNA Synthesis but Delays Maturation of Oligodendrocyte Progenitors", Journal of Neuroscience, vol. 21, No. 11, pp. 3849-3859 (2001).

(Continued)

*Primary Examiner*—David Romeo
*Assistant Examiner*—Daniel C Garnett
(74) *Attorney, Agent, or Firm*—Fish & Richardson P.C.

(57) ABSTRACT

This invention relates to a method of selectively producing neural cells, including neurons or glial cells, in vitro or in vivo. Also provided are methods of treating or ameliorating neurodegenerative disease or medical conditions by producing neural cells. Thus, a combination of factors is used to achieve two steps: increasing the number of neural stem cells and instructing the neural stem cells to selectively become neurons or glial cells.

22 Claims, 1 Drawing Sheet

OTHER PUBLICATIONS

Bernichtein, S., et al. S179D-human PRL, a pseudophosphorylated human PRL analog, is an agonist and not an antagonist. Endocrinology 142(9):3950-3963 (2001).

Fernandez-Pol, J.A. Epidermal growth factor receptor of A431 cells. Characterization of a monoclonal anti-receptor antibody noncompetitive agonist of epidermal growth factor action. J. Biol. Chem. 260(8):5003-5011 (1985).

Johnson, D.L., et al. Erythropoietin mimetic peptides and the future. Nephrol. Dial. Transplant. 15(9):1274-1277 (2000).

Kaushansky, K. Hematopoietic growth factor mimetics. Ann. N.Y. Acad. Sci. 938:131-138 (2001).

Kolb, B., et al. Nerve growth factor treatment prevents dendritic atrophy and promotes recovery of function after cortical injury. Neuroscience 76(4):1139-1151 (1997).

Livnah, O., et al. Functional mimicry of a protein hormone by a peptide agonist: the EPO receptor complex at 2.8 A. Science 273(5274):464-471 (1996).

Mode, A., et al. The human growth hormone (hGH) antagonist G120RhGH does not antagonize GH in the rat, but has paradoxical agonist activity, probably via the prolactin receptor, Endocrinology 137(2):447-454 (1996).

Moro, O., et al. Maxadilan, the vasodilator from sand flies, is a specific pituitary adenylate cyclase activating peptide type I receptor agonist. J. Biol. Chem. 272(2):966-70 (1997).

Rochefort, C., et al. Enriched odor exposure increases the number of newborn neurons in the adult olfactory bulb and improves odor memory. J. Neurosci. 22(7):2679-2689 (2002).

Shimazaki, T., et al. The ciliary neurotrophic factor/leukemia inhibitory factor/gp130 receptor complex operates in the maintenance of mammalian forebrain neural stem cells. J. Neurosci. 21(19):7642-7653 (2001), Oct.

Shingo, T., et al. Erythropoietin regulates the in vitro and in vivo production of neuronal progenitors by mammalian forebrain neural stem cells. J. Neurosci. 21(24):9733-9743 (2001), Dec.

Wrighton, N.C., et al. Small peptides as potent mimetics of the protein hormone erythropoietin. Science 273(5274):458-464 (1996).

* cited by examiner

COMBINED REGULATION OF NEURAL CELL PRODUCTION

RELATED APPLICATIONS

This application claims the benefit of U.S. Provisional Applications Ser. No. 60/316,365, filed Aug. 30, 2001; Ser. No. 60/316,579, filed Aug. 31, 2001; Ser. No. 60/322,514, filed Sep. 14, 2001; and Ser. No. 60/386,404, filed Jun. 7, 2002. The entire disclosure of each of these priority applications is hereby incorporated by reference.

FIELD OF THE INVENTION

This invention relates to a method of selectively producing neural cells, such as neurons or glial cells, in vitro or in vivo. Also provided are methods of treating or ameliorating neurodegenerative disease or medical conditions by producing neural cells.

REFERENCES

U.S. Patent Application Publication No. 2002 0098178 A1.
- U.S. Pat. No. 5,023,252.
- U.S. Pat. No. 5,128,242.
- U.S. Pat. No. 5,198,542.
- U.S. Pat. No. 5,208,320.
- U.S. Pat. No. 5,268,164.
- U.S. Pat. No. 5,326,860.
- U.S. Pat. No. 5,506,107.
- U.S. Pat. No. 5,506,206.
- U.S. Pat. No. 5,527,527.
- U.S. Pat. No. 5,547,935.
- U.S. Pat. No. 5,614,184.
- U.S. Pat. No. 5,623,050.
- U.S. Pat. No. 5,686,416.
- U.S. Pat. No. 5,723,115.
- U.S. Pat. No. 5,750,376.
- U.S. Pat. No. 5,773,569.
- U.S. Pat. No. 5,801,147.
- U.S. Pat. No. 5,833,988.
- U.S. Pat. No. 5,837,460.
- U.S. Pat. No. 5,851,832.
- U.S. Pat. No. 5,885,574.
- U.S. Pat. No. 5,955,346.
- U.S. Pat. No. 5,977,307.
- U.S. Pat. No. 5,980,885.
- U.S. Pat. No. 6,015,555.
- U.S. Pat. No. 6,048,971.
- U.S. Pat. No. 6,191,106.
- U.S. Pat. No. 6,242,563.
- U.S. Pat. No. 6,329,508.
- U.S. Pat. No. 6,333,031.
- U.S. Pat. No. 6,413,952.
- U.S. Pat. No. 6,429,186.
- WO 96 40231.
- WO 97 48729.

Bernichtein, S., et al. S179D-human PRL, a pseudophosphorylated human PRL analog, is an agonist and not an antagonist. Endocrinology 142(9):3950–3963 (2001).

Fernandez-Pol, J. A. Epidermal growth factor receptor of A431 cells. Characterization of a monoclonal anti-receptor antibody noncompetitive agonist of epidermal growth factor action. J. Biol. Chem. 260(8):5003–5011 (1985).

Johnson, D. L., et al. Erythropoietin mimetic peptides and the future. Nephrol. Dial. Transplant. 15(9):1274–1277 (2000).

Kaushansky, K. Hematopoietic growth factor mimetics. Ann. N.Y. Acad. Sci. 938:131–138 (2001).

Kolb, B., et al. Nerve growth factor treatment prevents dendritic atrophy and promotes recovery of function after cortical injury. Neuroscience 76(4):1139–1151 (1997).

Livnah, O., et al. Functional mimicry of a protein hormone by a peptide agonist: the EPO receptor complex at 2.8 A. Science 273(5274):464–471 (1996).

Mode, A., et al. The human growth hormone (hGH) antagonist G120RhGH does not antagonize GH in the rat, but has paradoxical agonist activity, probably via the prolactin receptor. Endocrinology 137(2):447–454 (1996).

Moro, O., et al. Maxadilan, the vasodilator from sand flies, is a specific pituitary adenylate cyclase activating peptide type I receptor agonist. J. Biol. Chem. 272(2):966–70 (1997).

Rochefort, C., et al. Enriched odor exposure increases the number of newborn neurons in the adult olfactory bulb and improves odor memory. J. Neurosci. 22(7):2679–2689 (2002).

Shimazaki, T., et al. The ciliary neurotrophic factor/leukemia inhibitory factor/gp130 receptor complex operates in the maintenance of mammalian forebrain neural stem cells. J. Neurosci. 21(19):7642–7653 (2001).

Shingo, T.; et al. Erythropoietin regulates the in vitro and in vivo production of neuronal progenitors by mammalian forebrain neural stem cells. J. Neurosci. 21(24):9733–9743 (2001).

Wrighton, N. C., et al. Small peptides as potent mimetics of the protein hormone erythropoietin. Science 273(5274):458–464 (1996).

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND OF THE INVENTION

In recent years, neurodegenerative disease has become an important concern due to the expanding elderly population which is at greatest risk for these disorders. Neurodegenerative diseases include the diseases which have been linked to the degeneration of neural cells in particular locations of the central nervous system (CNS), leading to the inability of these cells to carry out their intended function. These diseases include Alzheimer's Disease, Multiple Sclerosis (MS), Huntington's Disease, Amyotrophic Lateral Sclerosis, and Parkinson's Disease. In addition, probably the largest area of CNS dysfunction (with respect to the number of affected people) is not characterized by a loss of neural cells but rather by abnormal functioning of existing neural cells. This may be due to inappropriate firing of neurons, or the abnormal synthesis, release, and processing of neurotransmitters. These dysfunctions may be the result of well studied and characterized disorders such as depression and epilepsy, or less understood disorders such as neurosis and psychosis. Moreover, brain injuries often result in the loss of neural cells, the inappropriate functioning of the affected brain region, and subsequent behavior abnormalities.

Consequently, it is desirable to supply neural cells to the brain to compensate for degenerate or lost neurons/glial cells in order to treat neurodegenerative diseases or conditions.

One approach to this end is to transplant neural cells into the brain of the patient. This approach requires a source of large amounts of neural cells, preferably from the same individual or a closely related individual such that host-versus-graft or graft-versus-host rejections can be minimized. As it is not practical to remove a large amount of neurons or glial cells from one person to transplant to another, a method to culture large quantity of neural cells is necessary for the success of this approach.

Another approach is to induce the production of neural cells in situ to compensate for the lost or degenerate cells. This approach requires extensive knowledge about whether it is possible to produce neural cells in brains, particularly adult brains, and how.

The development of techniques for the isolation and in vitro culture of multipotent neural stem cells (for example, see U.S. Pat. Nos. 5,750,376; 5,980,885; 5,851,832) significantly increased the outlook for both approaches. It was discovered that fetal brains can be used to isolate and culture multipotent neural stem cells in vitro. Moreover, in contrast to the long time belief that adult brain cells are not capable of replicating or regenerating brain cells, it was found that neural stem cells may also be isolated from brains of adult mammals. These stem cells, either from fetal or adult brains, are capable of self-replicating. The progeny cells can again proliferate or differentiate into any cell in the neural cell lineage, including neurons, astrocytes and oligodendrocytes. Therefore, these findings not only provide a source of neural cells which can be used in transplantations, but also demonstrate the presence of multipotent neural stem cells in adult brain and the possibility of producing neurons or glial cells from these stem cells in situ.

It is therefore desirable to develop methods of efficiently proliferating neural stem cells for two purposes: to obtain more stem cells and hence neural cells which can be used in transplantation therapies, and to identify methods which can be used to produce more stem cells in situ.

SUMMARY OF THE INVENTION

This invention relates to a two-step method of producing neural cells in vitro or in vivo. We discovered that neurogenesis and gliogenesis by multipotent neural stem cells (NSCs) involve proliferation and directed differentiation. As shown in FIG. 1, EGF (or its adult homolog TGFα) induces the self-renewal/expansion of the NSC population. The NSCs will undergo spontaneous differentiation in a default pathway to become glial precursor cells (GPCs). This spontaneous differentiation can be attenuated by ciliary neurotrophic factor (CNTF). GPCs will differentiate into the glial cells, which differentiation is promoted by EGF. Alternatively, NSCs can be instructed by EPO and/or PACAP/cAMP to differentiate to neuronal precursor cells (NPCs), which make neurons only.

Therefore, a two-step process can be used to produce neurons or glial cells: (1) increasing the number of NSCs; and (2) promoting differentiation of the NSCs to either neurons or glial cells by subjecting the NSCs to appropriate conditions which selectively promotes production of neurons or glial cells.

Accordingly, one aspect of the present invention provides a method for producing neuronal precursor cells or glial precursor cells, comprising:
(a) providing at least one neural stem cell;
(b) contacting the neural stem cell with a factor selected from the group consisting of prolactin, growth hormone, estrogen, ciliary neurotrophic factor (CNTF), pituitary adenylate cyclase activating polypeptide (PACAP), fibroblast growth factor (FGF), transforming growth factor alpha (TGFα) and epidermal growth factor (EGF) in an amount sufficient to increase the number of neural stem cells; and
(c) contacting the neural stem cells from step (b) to a factor selected from the group consisting of erythropoietin (EPO), PACAP, prolactin, serotonin, bone morphogenetic protein (BMP) and cAMP in an amount sufficient to enhance the production of neuronal precursor cells or glial precursor cells from the neural stem cells;
with the proviso that when the factor in step (b) is EGF or FGF, the factor in step (c) is PACAP or prolactin.

Thus, step (b) is performed to increase the number of neural stem cells, which can be achieved by at least one of the following:
(i) increasing proliferation of the neural stem cell, such as by providing EGF;
(ii) inhibiting spontaneous differentiation of the neural stem cell, such as by providing CNTF; or
(iii) promoting survival of the neural stem cell, such as by providing an estrogen.

These two steps, increasing NSCs numbers and enhancing neuron or glia production, may be performed sequentially or concurrently. It is preferable that step (b) is performed prior to step (c).

The factors can be provided by any method established in the art. For example, they can be administered intravascularly, intrathecally, intravenously, intramuscularly, subcutaneously, intraperitoneally, topically, orally, rectally, vaginally, nasally, by inhalation or into the brain. The administration is preferably performed systemically, particularly by subcutaneous administration. The factors can also be provided by administering to the mammal an effective amount of an agent that can increase the amount of endogenous factors in the mammal. For example, the level of prolactin in an animal can be increased by using prolactin releasing peptide.

When the factors are not directly delivered into the brain, a blood brain barrier permeabilizer can be optionally included to facilitate entry into the brain. Blood brain barrier permeabilizers are known in the art and include, by way of example, bradykinin and the bradykinin agonists described in U.S. Pat. Nos. 5,686,416; 5,506,206 and 5,268,164 (such as $NH_2$-arginine-proline-hydroxyproxyproline-glycine-thienylalanine-serine-proline-4-Me-tyrosineψ($CH_2NH$)-arginine-COOH). Alternatively, the factors can be conjugated to the transferrin receptor antibodies as described in U.S. Pat. Nos. 6,329,508; 6,015,555; 5,833,988 or 5,527,527. The factors can also be delivered as a fusion protein comprising the factor and a ligand that is reactive with a brain capillary endothelial cell receptor, such as the transferrin receptor (see, e.g., U.S. Pat. No. 5,977,307).

Although mammals of all ages can be subjected to this method, it is preferable that the mammal is not an embryo. More preferably, the mammal is an adult.

The mammal may suffer from or be suspected of having a neurodegenerative disease or condition. The disease or condition may be a brain injury, such as stroke or an injury caused by a brain surgery. The disease or condition may be aging, which is associated with a significant reduction in the number of neural stem cells. The disease or condition can also be a neurodegenerative disease, particularly Alzheimer's disease, multiple sclerosis, Huntington's disease, amyotrophic lateral sclerosis, or Parkinson's disease.

Alternatively, the neural stem cell may be in a culture in vitro. The cell may be from an animal of any age. Preferably, the animal is not an embryo, and most preferably the animal is an adult.

Another aspect of the present invention provides a method of treating or ameliorating a neurodegenerative disease or medical condition, comprising (a) administering to a mammal a factor which is capable of increasing the number of neural stem cells; and (b) subjecting the mammal to a condition which enhances the production of a lineage restricted cell; whereby production of the lineage restricted cell is enhanced. For example, neurons can be produced to compensate for lost or malfunctioning neurons by administering EGF and EPO. Other factors which are capable of increasing the number of NSCs, such as CNTF, FGF, prolactin, growth hormone, IGF-1, PACAP or estrogen, can also be used instead of EGF or in addition to EGF. Likewise, other factors which can enhance neuron production, such as PACAP or factors which increases cAMP level, can be used in the place of EPO or in addition to EPO.

To produce glial cells to compensate for lost or malfunctioning glial cells, EGF can be administered, which stimulates NSC proliferation, and the resulting NSC will differentiate to glial cells by default. Optionally, inhibitors of the neuronal pathway, such as antibodies of EPO and cAMP signaling inhibitors, can be used to promote glial production. Preferably, a factor that promotes glial formation, such as BMP, is also used to further produce glial cells.

DETAILED DESCRIPTION OF THE INVENTION

Figure 1:
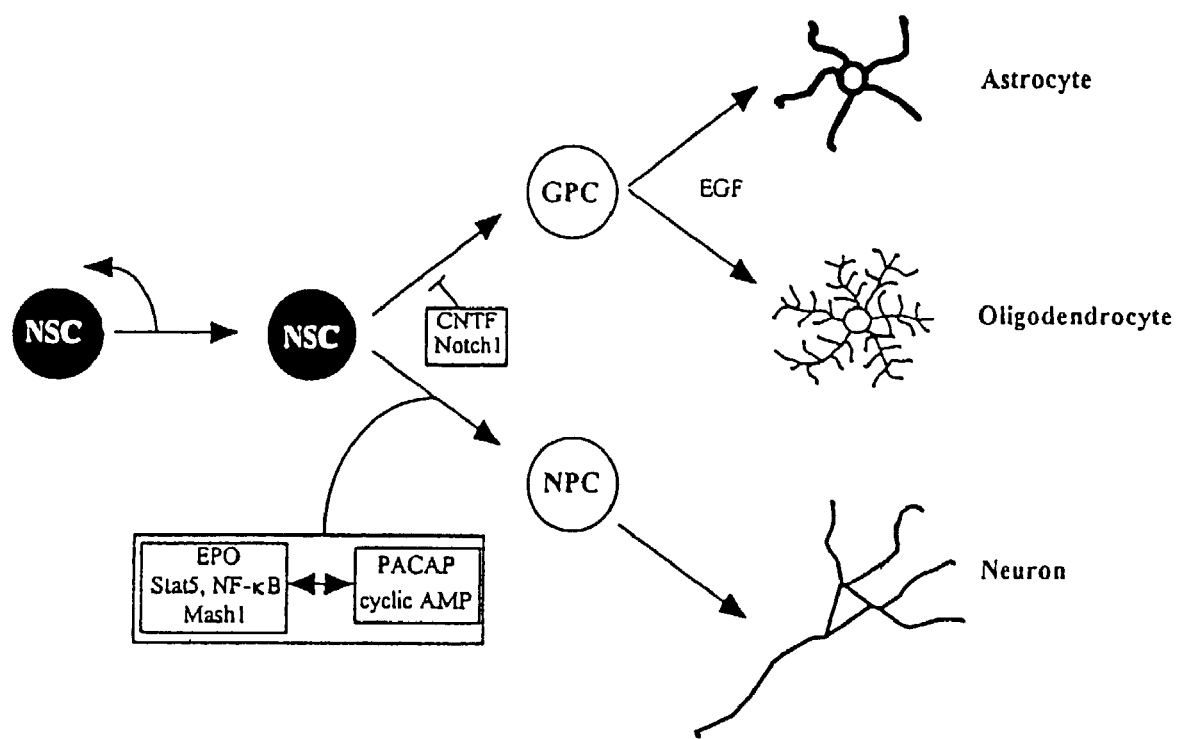
FIG. 1 diagrams a model for neurogenesis and gliogenesis by neural stem cells (NSCs). EGF (or its adult homolog TGFα) induces the self-renewal/expansion of the NSC population. The NSCs will undergo spontaneous differentiation as a default pathway to become glial precursor cells (GPCs). This spontaneous differentiation can be attenuated by CNTF. GPCs differentiate into astrocytes and/or oligodentrocytes, which differentiation is promoted by EGF. Alternatively, NSCs can be instructed by EPO and/or PACAP/cAMP to differentiate to neuronal precursor cells (NPCs), which make neurons only.

This invention relates to a method of selectively producing neural cells, including neurons or glial cells, in vitro or in vivo. Also provided are methods of treating or ameliorating neurodegenerative disease or medical conditions by producing neural cells. Thus, a combination of factors is used to achieve two steps: increasing the number of neural stem cells and instructing the neural stem cells to selectively become neurons or glial cells.

Prior to describing the invention in further detail, the terms used in this application are defined as follows unless otherwise indicated.

Definitions

A "neural stem cell" is a stem cell in the neural cell lineage. A stem cell is a cell which is capable of reproducing itself. In other words, daughter cells which result from stem cell divisions include stem cells. The neural stem cells are capable of ultimately differentiating into all the cell types in the neural cell lineage, including neurons, astrocytes and oligodendrocytes (astrocytes and oligodendrocytes are collectively called glia or glial cells). Thus, the neural stem cells referred to herein are multipotent neural stem cells.

A "neurosphere" is a group of cells derived from a single neural stem cell as the result of clonal expansion. A "primary neurosphere" refers to the neurospheres generated by plating as primary cultures brain tissue which contains neural stem cells. The method for culturing neural stem cells to form neurospheres has been described in, for example, U.S. Pat. No. 5,750,376. A "secondary neurosphere" refers to the neurospheres generated by dissociating primary neurospheres and allowing the individual dissociated cells to form neurospheres again.

A "neural cell" is any cell in the neural lineage. Preferably a neural cell is a neuron or glial cell.

A polypeptide which shares "substantial sequence similarity" with a native factor is at least about 30% identical with the native factor at the amino acid level. The polypeptide is preferably at least about 40%, more preferably at least about 60%, yet more preferably at least about 70%, and most preferably at least about 80% identical with the native factor at the amino acid level.

The phrase "percent identity" or "% identity" of an analog or variant with a native factor refers to the percentage of amino acid sequence in the native factor which are also found in the analog or variant when the two sequences are aligned. Percent identity can be determined by any methods or algorithms established in the art, such as LALIGN or BLAST.

A polypeptide possesses a "biological activity" of a native factor if it is capable of binding to the receptor for the native factor or being recognized by a polyclonal antibody raised against the native factor. Preferably, the polypeptide is capable of specifically binding to the receptor for the native factor in a receptor binding assay.

A "functional agonist" of a native factor is a compound that binds to and activates the receptor of the native factor, although it does not necessarily share a substantial sequence similarity with the native factor.

A "prolactin" is a polypeptide which (1) shares substantial sequence similarity with a native mammalian prolactin, preferably the native human prolactin, a 199-amino acid polypeptide synthesized mainly in the pituitary gland; and (2) possesses a biological activity of the native mammalian prolactin. Thus, the term "prolactin" encompasses prolactin analogs which are the deletional, insertional, or substitutional mutants of the native prolactin. Furthermore, the term "prolactin" encompasses the prolactins from other species and the naturally occurring variants thereof.

In addition, a "prolactin" may also be a functional agonist of a native mammalian prolactin receptor. For example, the functional agonist may be an activating amino acid sequence disclosed in U.S. Pat. No. 6,333,031 for the prolactin receptor; a metal complexed receptor ligand with agonist activities for the prolactin receptor (U.S. Pat. No. 6,413,952); G120RhGH, which is an analog of human growth hormone but acts as a prolactin agonist (Mode et al., 1996); or a ligand for the prolactin receptor as described in U.S. Pat. Nos. 5,506,107 and 5,837,460.

An "EGF" means a native EGF or any EGF analog or variant that shares a substantial amino acid sequence similarity with a native EGF, as well as at least one biological activity with the native EGF, such as binding to the EGF receptor. Particularly included as an EGF is the native EGF of any species, TGFα, or recombinant modified EGF. Specific examples include, but are not limited to, the recombinant modified EGF having a deletion of the two C-terminal amino acids and a neutral amino acid substitution at position 51 (particularly EGF51gln51; U.S. Patent Application Publication No. 20020098178A1), the EGF mutein (EGF-$X_{16}$) in which the His residue at position 16 is replaced with a neutral or acidic amino acid (U.S. Pat. No. 6,191,106), the 52-amino acid deletion mutant of EGF which lacks the amino terminal residue of the native EGF (EGF-D), the EGF deletion mutant in which the N-terminal residue as well as the two C-terminal residues (Arg-Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in U.S. Patent Application Publication No. 20020098178A1, and U.S. Pat. Nos. 6,191,106 and 5,547,935.

In addition, an "EGF" may also be a functional agonist of a native mammalian EGF receptor. For example, the functional agonist may be an activating amino acid sequence disclosed in U.S. Pat. No. 6,333,031 for the EGF receptor, or an antibody that has agonist activities for the EGF receptor (Fernandez-Pol, 1985 and U.S. Pat. No. 5,723,115).

A "PACAP" means a native PACAP or any PACAP analog or variant that shares a substantial amino acid sequence similarity with a native PACAP, as well as at least one biological activity with the native PACAP, such as binding to the PACAP receptor. Useful PACAP analogs and variants include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563.

In addition, a "PACAP" may also be a functional agonist of a native mammalian PACAP receptor. For example, the functional agonist may be maxadilan, a polypeptide that acts as a specific agonist of the PACAP type-1 receptor (Moro et al., 1997).

An "erythropoietin (EPO)" means a native EPO or any EPO analog or variant that shares a substantial amino acid sequence similarity with a native EPO, as well as at least one biological activity with the native EPO, such as binding to the EPO receptor. Erythropoietin analogs and variants are disclosed, for example, in U.S. Pat. Nos. 6,048,971 and 5,614,184.

In addition, an "EPO" may also be a functional agonist of a native mammalian EPO receptor. For example, the functional agonist may be EMP1 (EPO mimetic peptide 1, Johnson et al., 2000); one of the short peptide mimetics of EPO as described in Wrighton et al., 1996 and U.S. Pat. No. 5,773,569; any small molecular EPO mimetic as disclosed in Kaushansky, 2001; an antibody that activates the EPO receptor as described in U.S. Pat. No. 5,885,574, WO 96/40231, WO 97/48729, Fernandez-Pol, 1985 or U.S. Pat. No. 5,723,115; an activating amino acid sequence as disclosed in U.S. Pat. No. 6,333,031 for the EPO receptor; a metal complexed receptor ligand with agonist activities for the EPO receptor (U.S. Pat. No. 6,413,952), or a ligand for the EPO receptor as described in U.S. Pat. Nos. 5,506,107 and 5,837,460.

"Enhancing" or "promoting" the formation of a cell type means increasing the number of the cell type. Thus, a factor can be used to enhance neuron formation if the number of neurons in the presence of the factor is larger than the number of neurons absent the factor. The number of neurons in the absence of the factor may be zero or more.

A "neurodegenerative disease or condition" is a disease or medical condition associated with neuron loss or dysfunction. Examples of neurodegenerative diseases or conditions include neurodegenerative diseases, brain injuries or CNS dysfunctions. Neurodegenerative diseases include, for example, Alzheimer's disease, multiple sclerosis (MS), macular degeneration, glaucoma, diabetic retinopathy, peripheral neuropathy, Huntington's disease, amyotrophic lateral sclerosis, and Parkinson's disease. Brain injuries include, for example, stroke (e.g., hemorrhagic stroke, focal ischemic stroke or global ischemic stroke) and traumatic brain injuries (e.g. injuries caused by a brain surgery or physical accidents). CNS dysfunctions include, for example, depression, epilepsy, neurosis and psychosis.

"Treating or ameliorating" means the reduction or complete removal of the symptoms of a disease or medical condition.

A mammal "suspected of having a neurodegenerative disease or condition" is a mammal which is not officially diagnosed with the neurodegenerative disease or condition but shows a symptom of the neurodegenerative disease or condition, is susceptible to the neurodegenerative disease or condition due to family history or genetic predisposition, or has previously had the neurodegenerative disease or condition and is subject to the risk of recurrence.

"Transplanting" a composition into a mammal refers to introducing the composition into the body of the mammal by any method established in the art. The composition being introduced is the "transplant", and the mammal is the "recipient". The transplant and the recipient may be syngeneic, allogeneic or xenogeneic. Preferably, the transplantation is an autologous transplantation.

An "effective amount" is an amount of a therapeutic agent sufficient to achieve the intended purpose. For example, an effective amount of a factor to increase the number of neural stem cells is an amount sufficient, in vivo or in vitro, as the case may be, to result in an increase in neural stem cell number. An effective amount of a composition to treat or ameliorate a neurodegenerative disease or condition is an amount of the composition sufficient to reduce or remove the symptoms of the neurodegenerative disease or condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Methods

Neural stem cells (NSCs), such as the ones found in the adult forebrain, are the likely source of restricted neuronal and glial progenitors, which repopulate structures such as the olfactory bulb and corpus callosum, respectively. The mechanisms by which NSCs give rise to restricted progenitors have been unclear prior to this invention.

We found that EGF-responsive NSCs gradually become restricted to a glial lineage. This process is blocked by CNTF, acting through notch1, to maintain NSCs in a multipotent stage. We also found that erythropoietin (EPO) directs the production of restricted neuronal precursors through a mechanism that utilizes Mash1.

Thus, we infused either CNTF or EPO into the lateral ventricles of adult mice for six days, after which we either removed the entire adult ependyma/subependyma to examine the total number of EGF-responsive NSCs or examined the in vivo production of neuronal precursors. CNTF infusion resulted in a 20–25% increase in the number of NSCs, most likely by preventing NSC differentiation into glial precursors. EPO infusion resulted in a 50% reduction in the number of NSCs and a concomitant doubling in neuronal precursors. Infusion of anti-EPO antibodies resulted in a 20% increase in NSCs. Therefore, EGF-responsive NSCs turn over continuously in vivo, a sub-population of which spontaneously differentiates into restricted glial precursors, while another sub-population is directed to the neuronal restricted linage by EPO.

This mechanism is illustrated in FIG. 1. Thus, EGF (or its adult homolog TGFα) induces the self-renewal/expansion of the NSC population. The NSCs undergo spontaneous differentiation as a default pathway to become glial precursor cells (GPCs), which differentiate into glial cells. This spontaneous differentiation can be attenuated by CNTF. Alternatively, NSCs can be instructed by EPO and/or PACAP/cAMP to differentiate to neuronal precursor cells (NPCs), which make neurons only.

Based on this mechanism, we developed a two-step method to produce neural cells. The first step is to increase the number of neural stem cells, which can be achieved by, for example, proliferating neural stem cells (e.g., by EGF, FGF-1, FGF-2, TGFα, estrogen, prolactin, PACAP, growth hormone, and/or IGF-1), inhibiting spontaneous differentiation of neural stem cells (e.g., by CNTF), and/or promoting survival of neural stem cells (e.g., by estrogen). The second step is to enhance neuronal or glial formation from neural stem cells. For example, erythropoietin, prolactin, serotonin, PACAP and/or cyclic AMP can be used to enhance neuron formation, while bone morphogenetic protein (BMP) can be used to enhance glial formation.

The present method can be used in vivo or in vitro. In vitro, the present invention will result in large quantities of neural cells, which can be used in research or therapeutical purposes. In particular, the neural cells can be used in transplantation treatment for neurodegenerative diseases or conditions. In vivo, the present method can increase the number of neural stem cells in situ, and enhance neuronal or glial formation from the enlarged pool of neural stem cells. The resulting neural cells can migrate to appropriate places in the nervous system to enhance neurological functions, or compensate for lost or dysfunctional neural cells. In addition, the in vivo and in vitro applications can be combined. Thus, neural cells, particularly neural stem cells produced by the present method in vitro, can be transplanted into an animal, and factors of the second step can be provided to the animal to enhance differentiation of neural cells in vivo. Optionally, factors of the first step may be provided to the animal as well to further increase the number of neural stem cells that can be subsequently turned to neurons or glial cells.

One particularly interesting neurodegenerative condition is aging. We have found that the number of neural stem cells in the subventricular zone is significantly reduced in aged mice. Accordingly, it will be of particular interest to ameliorate problems associated with aging by the present invention.

In addition, the neural stem cell in the subventricular zone is the source of olfactory neurons, and olfactory dysfunction is a hallmark of forebrain neurodegenerative diseases, such as Alzheimer's, Parkinson's and Huntington's diseases. Disruption of neuronal migration to the olfactory bulb leads to deficits in olfactory discrimination, and doubling the new olfactory interneuons enhances new odor memory (Rochefort et al., 2002). Therefore, the present invention can be used to enhance olfactory discrimination or olfactory memory, as well as physiological functions that are associated with olfaction and olfactory discrimination, such as mating, offspring recognition and rearing.

Another particularly important application of the present invention is the treatment and/or amelioration of brain injuries, such as stroke (Example 2). A brain injury mimicking a stroke was introduced into the motor cortex of rats, and the injured rats showed abnormal behavioral conducts that correlated with the location of the injury. The rats then received prolactin or growth hormone for 7 days, both of which can increase neural stem cell proliferation. Subsequently, the rats received a vehicle control or erythropoietin for 7 days to enhance neuron formation. The rats were then observed for a period of time for behavioral testing, and sacrificed for anatomical analysis.

The results indicate that both prolactin and growth hormone treatments led to an improvement of motor functions in the injured rats. The addition of erythropoietin further enhanced the effect, particularly when combined with prolactin. The anatomical analysis also shows that the number of migrating neurons and/or neural stem cells was increased by every treatment comprising prolactin or growth hormone. In fact, the combination of prolactin and erythropoietin even resulted in complete or partial filling of the cavities created by the brain injury in a majority of the rats. Therefore, these factors, particular combinations of which, can be used to produce neural cells and restore neurological functions in animals with brain injuries.

An intriguing observation is that prolactin and growth hormone led to the restoration of different behavioral functions. Thus, the rats recovered from asymmetrical forelimb usage in balancing after receiving growth hormone, while prolactin acted to correct abnormal positioning of the forelimb during swimming. Therefore, different factors may lead to different cellular migration patterns or the production of different cells, which participate in different neural functions. Accordingly, it is preferable that multiple factors are combined in the treatment of diseases or conditions that have complicated symptoms. Preferred combinations include:

(a) prolactin and at least one factor that enhances neuronal or glial differentiation, such as EPO, PACAP, cyclic AMP and/or BMP;

(b) EGF and at least one factor that enhances neuronal or glial differentiation, such as prolactin, EPO, PACAP, cyclic AMP and/or BMP, particularly prolactin and/or PACAP;

(c) at least one factor that increases neural stem cell number in conjunction with prolactin;

(d) at least one factor that increases neural stem cell number in conjunction with PACAP;

(e) at least one factor that increases neural stem cell number in conjunction with EPO; and (f) combinations of the above.

Particularly preferred combinations include EGF and EPO, EGF and prolactin, EGF and PACAP, EGF and growth hormone (and/or IGF-1), EGF and prolactin and growth hormone (and/or IGF-1), EGF and prolactin and PACAP, prolactin and growth hormone (and/or IGF-1), prolactin and growth hormone (and/or IGF-1) and EPO, prolactin and PACAP and growth hormone (and/or IGF-1). Most preferred combinations include EGF and PACAP, EGF and prolactin, and prolactin and PACAP. Preferably, FGF is not used.

Compositions

The present invention provides compositions comprising at least one factor that is capable of increasing neural stem cell numbers and at least one factor that is capable of enhancing differentiation of neural stem cells. It should be noted that some factors are capable of both functions, such prolactin. PACAP, in addition to enhancing neuronal differentiation, also enhances proliferation of neural stem cells in the presence of another mitogen.

The factors that are useful in the present invention include their analogs and variants that share a substantial similarity and at least one biological activity with the native factors. For example, although the major form of prolactin found in the pituitary gland has a molecular weight of 23 kDa, variants of prolactin have been characterized in many mammals, including humans. Prolactin variants can result from alternative splicing of the primary transcript, proteolytic cleavage and other post-translational modifications. A prolactin variant of 137 amino acids has been described in the anterior pituitary, which is likely to be a product of alternative splicing. A variety of proteolytic products of prolactin have been characterized, particularly the 14-, 16- and 22-kDa prolactin variants, all of which appear to be prolactin fragments truncated at the C-terminus. Other post-translational modification reported for prolactin include dimerization, polymerization, phosphorylation, glycosylation, sulfation and deamidation.

The prolactin useful in the present invention includes any prolactin analog, variant or prolactin-related protein which is capable of increasing neural stem cell number. A prolactin analog or variant is a polypeptide which contains at least about 30% of the amino acid sequence of the native human prolactin, and which possesses a biological activity of prolactin. Preferably, the biological activity of prolactin is the ability to bind prolactin receptors. Although several isoforms of the prolactin receptor have been isolated, for example the long, intermediate and short forms in rat, the isoforms share the same extracellular domain which binds prolactin. Therefore, any receptor isoform can be used to assay for prolactin binding activity. Specifically included as prolactins are the naturally occurring prolactin variants, prolactin-related protein, placental lactogens, S1179D-human prolactin (Bernichtein et al., 2001), prolactins from various mammalian species, including but not limited to, human, other primates, rat, mouse, sheep, pig, and cattle, and the prolactin mutants described in U.S. Pat. Nos. 6,429,186 and 5,955,346.

Similarly, in addition to native EGF, an EGF analog or variant can also be used, which should share a substantial amino acid sequence similarity with the native EGF, as well as at least one biological activity with the native EGF, such as binding to the EGF receptor. Particularly included as an EGF is the native EGF of any species, TGFα, or recombinant modified EGF. Specific examples include, but are not limited to, the recombinant modified EGF having a deletion of the two C-terminal amino acids and a neutral amino acid substitution at position 51 (particularly EGF51gln51; U.S. Patent Application Publication No. 20020098178A1), the EGF mutein (EGF-$X_{16}$) in which the His residue at position 16 is replaced with a neutral or acidic amino acid (U.S. Pat. No. 6,191,106), the 52-amino acid deletion mutant of EGF which lacks the amino terminal residue of the native EGF (EGF-D), the EGF deletion mutant in which the N-terminal residue as well as the two C-terminal residues (Arg-Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in U.S. Patent Application Publication No. 20020098178A1, and U.S. Pat. Nos. 6,191,106 and 5,547,935.

As another example, useful PACAP analogs and variants include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563.

Erythropoietin analogs and variants are disclosed, for example, in U.S. Pat. Nos. 6,048,971 and 5,614,184.

Further contemplated in the present invention are functional agonists of prolactin or additional factors useful in the present invention. These functional agonists bind to and activate the receptor of the native factor, although they do not necessarily share a substantial sequence similarity with the native factor. For example, maxadilan is a polypeptide that acts as a specific agonist of the PACAP type-1 receptor (Moro et al., 1997).

Functional agonists of EPO have been extensively studied. EMP1 (EPO mimetic peptide 1) is one of the EPO mimetics described in Johnson et al., 2000. Short peptide mimetics of EPO are described in, e.g., Wrighton et al., 1996 and U.S. Pat. No. 5,773,569. Small molecular EPO mimetics are disclosed in, e.g., Kaushansky, 2001. Antibodies that activate the EPO receptor are described in, e.g., U.S. Pat. No. 5,885,574; WO 96/40231 and WO 97/48729).

Antibodies that have agonist activities for the EGF receptor are described, e.g., in Fernandez-Pol, 1985 and U.S. Pat. No. 5,723,115. In addition, activating amino acid sequences are also disclosed in U.S. Pat. No. 6,333,031 for the EPO receptor, EGF receptor, prolactin receptor and many other cell surface receptors; metal complexed receptor ligands with agonist activities for the prolactin and EPO receptors can be found in U.S. Pat. No. 6,413,952. Other methods of identifying and preparing ligands for receptors, e.g., EPO and prolactin receptors, are described, for example, in U.S. Pat. Nos. 5,506,107 and 5,837,460.

It should be noted that the effective amount of each analog, variant or functional agonist may be different from that for the native factor or compound, and the effective amount in each case can be determined by a person of ordinary skill in the art according to the disclosure herein. Preferably, the native factors, or analogs and variants that share substantial sequence similarity with the native factors, are used in the present invention.

Pharmaceutical compositions are also provided, comprising the factors as described above, and a pharmaceutically acceptable excipient and/or carrier.

The pharmaceutical compositions can be delivered via any route known in the art, such as parenterally, intrathecally, intravascularly, intravenously, intramuscularly, transdermally, intradermally, subcutaneously, intranasally, topically, orally, rectally, vaginally, pulmonarily or intraperitoneally. Preferably, the composition is delivered into the central nervous system by injection or infusion. More preferably it is delivered into a ventricle of the brain, particularly the lateral ventricle. Alternatively, the composition is preferably delivered by systemic routes, such as subcutaneous administration. For example, we have discovered that prolactin, growth hormone, IGF-1, PACAP and EPO can be effectively delivered by subcutaneous administration to modulate the number of neural stem cells in the subventricular zone.

When the composition is not directly delivered into the brain, and factors in the composition do not readily cross the blood brain barrier, a blood brain barrier permeabilizer can be optionally included to facilitate entry into the brain. Blood brain barrier permeabilizers are known in the art and include, by way of example, bradykinin and the bradykinin agonists described in U.S. Pat. Nos. 5,686,416; 5,506,206 and 5,268,164 (such as NH$_2$-arginine-proline-hydroxyproxyproline-glycine-thienylalanine-serine-proline-4-Me-tyrosineψ(CH$_2$NH)-arginine-COOH). Alternatively, the factors can be conjugated to the transferrin receptor antibodies as described in U.S. Pat. Nos. 6,329,508; 6,015,555; 5,833,988 or 5,527,527. The factors can also be delivered as a fusion protein comprising the factor and a ligand that is reactive with a brain capillary endothelial cell receptor, such as the transferrin receptor (see, e.g., U.S. Pat. No. 5,977,307).

The pharmaceutical compositions can be prepared by mixing the desired therapeutic agents with an appropriate vehicle suitable for the intended route of administration. In making the pharmaceutical compositions of this invention, the therapeutic agents are usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the therapeutic agent. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the therapeutic agents, soft and hard gelatin capsules, suppositories, sterile injectable solutions, and sterile packaged powders.

Some examples of suitable excipients include artificial cerebral spinal fluid, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the therapeutic agents after administration to the patient by employing procedures known in the art.

For preparing solid compositions such as tablets, the therapeutic agent is mixed with a pharmaceutical excipient to form a solid preformulation composition containing a homogeneous mixture of a compound of the present invention. When referring to these preformulation compositions as homogeneous, it is meant that the therapeutic agents are dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. The compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another formulation employed in the methods of the present invention employs transdermal delivery devices ("patches"). Such transdermal patches may be used to provide continuous or discontinuous infusion of the therapeutic agent of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*.

The following abbreviations have the following meanings. Abbreviations not defined have their generally accepted meanings.

| | |
|---|---|
| EGF = | epidermal growth factor |
| PDGF = | platelet derived growth factor |
| DMSO = | dimethylsulfoxide |
| CNTF = | ciliary neurotrophic factor |
| EPO = | erythropoietin |
| NSC = | neural stem cell |
| GPC = | glial precursor cell |
| NPC = | neuronal precursor cell |
| PACAP = | pituitary adenylate cyclase activating polypeptide |
| cAMP = | cyclic AMP |

Materials and Methods

Neural Stem Cell Culture

The protocols for neural stem cell culture are described in detail in U.S. Pat. No. 5,750,376 or Shingo et al., 2001. Briefly, embryonic neural stem cells were prepared from E14 medial and lateral ganglionic eminences. Adult neural stem cells were prepared from the subventricular zone of adult mice. The tissue was cultured in basal medium containing 20 ng/ml EGF, or other growth factors as indicated in each case, to form neurospheres. The composition of the basal medium is as follows: DMEM/F12 (1:1); glucose (0.6%); glutamine (2 mM); sodium bicarbonate (3 mM); HEPES (5 mM); insulin (25 μg/ml); transferrin (100 μg/ml); progesterone (20 nM); putrescine (60 μM); and selenium chloride (30 nM).

Seven days later, the neurospheres (primary neurospheres) were passaged by mechanical dissociation and reseeded as single cells (passage 1). For secondary neurospheres, the single cells were then cultured for seven days to form secondary neurospheres.

Infusion of Growth Factors

Two-month-old CD-1 mice (Charles-River, Laval, Quebec, Canada) were anesthetized with sodium pentobarbital (120 mg/kg, i.p.) and implanted with an osmotic pump (Alzet 1007D; Alza Corporation, Palo Alto, Calif.). The cannula was located in the right lateral ventricle (anteroposterior+0.2 mm, lateral +0.8 mm to bregma, and dorsoventral −2.5 mm below dura with the skull leveled between lambda and bregma). Human recombinant EPO (1000 I U/ml), rabbit anti-EPO neutralizing antibody (100 µg/ml), rabbit IgG (100 µg/ml), rat recombinant CNTF (33 µg/ml), or human recombinant EGF (33 µg/ml) was dissolved in 0.9% saline containing 1 mg/ml mouse serum albumin (Sigma). Each animal was infused for 6 consecutive days at a flow rate of 0.5 µl/hr, resulting in a delivery of about 25 IU of EPO, 3 µg of antibodies, or 400 ng of CNTF or EGF per day.

Test Animals for the Stroke Study

Adult male Long-Evans rats (250–350 g) were obtained from Charles River Breeding Farms and were adapted to the colony for two weeks prior to any treatment. A week before surgery the rats were given a baseline testing on the behavioral tests.

Focal Ischemic Injury and Infusion

The animals for the stroke study received unilateral devascularization of the sensorimotor cortex. Using Isoflurane anesthesia, the skin was incised and retracted and the overlying fascia were removed from the skull. A skull opening was made at the following coordinates, taking care not to damage the dura: AP +4.0 to −2.0; L 1.5 to 4 (the parasagittal ridge; Kolb et al., 1997). The dura was cut and retracted from the skull opening. A cotton swab soaked in sterile saline was gently rubbed across the exposed pia and the vessels were removed. A hole was then drilled in the contralateral hemisphere to provide an opening for the cannulae attached to the osmotic minipump at AP-0.5; L 1.5. An osmotic minipump was placed under the skin between the shoulder blades and a tube connected under the skin to the cannulae, which was attached to the skull with fast-drying cement. Once hemostasis had been achieved the scalp was sutured closed with 5-O sterile suture. The animals were given a single injection of Banamine (an analgesic) and returned to their home cage. Sham animals received only anesthesia, the bone opening, and the skin was incised and sutured.

Six days later the animals were assessed using the behavioral test. On the following day the animals were re-anesthetized and the minipump was replaced with a second one containing the appropriate solutions. Sham animals were only anesthetized. The animals were retested 7, 14, and 28 days later to yield behavioral measures on weeks 1,2,3,4, and 6.

Forelimb Inhibition Test

This test has been shown to constitute a sensitive measure of functional integrity of regions of anterior neocortex. In normal rats, swimming is accomplished by propulsion from the hind limbs. The forelimbs are normally inhibited from any stroking and are held immobile and together under the animal's neck. Inhibition of the forelimbs was assessed by filming animals while swimming. Animals were introduced into one end of an aquarium (30 w×90 l×43 h cm) filled to a depth of 25 cm with room temperature water (~25° C.) and filmed as they swim to a 9.5 cm square visible platform. This platform projects 2 cm above the surface of the water and is positioned at the opposite end of the aquarium. Scoring of inhibition was done by counting the number of strokes, if any, made by each forelimb in three swims along the length of the aquarium. A swim was deemed scorable only if the animal did not touch the sides of the aquarium during the swimming trial.

Forelimb Asymmetry Test

Forepaw asymmetry of the animals was determined by filming them from below while in an acrylic cylinder 25 cm in diameter, on an acrylic platform. Preference was determined by separately counting the number of times in 5 minutes that an animal reared and placed the left or right forepaw on the surface of the cylinder in a gesture of postural stabilization. This test allows a measure of asymmetry in forelimb use, a measure that shows a reliable bias to using the limb ipsilateral to the injury.

Brain Anatomical Analysis

At the conclusion of week 6 the animals were given an overdose of Euthanol and intracardially perfused with 0.9% saline and 4% paraformaldehyde in picric acid. The brains were cryoprotected and cut on a Vibratome at 40 microns. Five sets of sections were kept every 400 microns. Two sets were stained, one with Cresyl Violet and one with Doublecortin. The remaining sets were saved. The Cresyl Violet staining was performed on the slides whereas the Doublecortin was performed as an immunohistochemical procedure on free-floating sections. The Cresyl Violet staining allows assessment of lesion extent whereas the Doublecortin stains for a microtubule associated protein that is present in migrating neuronal progenitor cells.

EXAMPLE 1

The Effect of CNTF and EPO In Vivo

To determine the effect of CNTF and EPO in vivo, CNTF or EPO was infused into adult mice for six days as described in Materials and Methods. The brain tissue was then harvested and used to grow neural stem cells as an indication of the number of neural stem cells in the brain after infusion. Alternatively, the brain tissue was stained for tyrosine hydroxylase or Mash1 to determine the extent of neurogenesis.

As described in detail in Shimazaki et al., 2001, CNTF infusion led to a significant increase of the number of primary neurospheres that can be obtained from the brain (about 25%). Moreover, coinfusion of EGF and CNTF increased the number of neural stem cells by about 40%. Therefore, CNTF is capable of increasing neural stem cell numbers, particularly in combination with EGF. CNTF does not stimulate proliferation of neural stem cells, however, as CNTF did not increase the number of BrdU positive cells when BrdU was also given to the animals.

Since CNTF does not promote proliferation or survival of neural stem cells, we hypothesized that CNTF inhibits spontaneous differentiation of neural stem cells. By spontaneously differentiating into a lineage-restricted cell, neural stem cell will not be able to self-renew, and the number of neural stem cells will decrease while the number of differentiated cells increase. Therefore, if CNTF inhibits this spontaneous differentiation, a neurosphere produced in the presence of CNTF should be more expandable and multipotent than a neurosphere produced in its absence.

Accordingly, we compared the expandability and multipotency of neurospheres that were produced in EGF alone or EGF plus CNTF. For expandability, pass 1 neurospheres were dissociated and replated at clonal density to generate pass 2 neurospheres, and the number of pass 2 neurospheres that were derived from a single pass 1 sphere was counted. The results show that the pass 1 neurospheres generated in EGF plus CNTF led to significantly more pass 2 spheres, indicating that these pass 1 spheres contained more expandable cells than spheres generated in EGF alone. For multipotency, the percentages of neuron, oligodendrocyte and astrocyte that could be derived from each neurosphere were determined, and the results show that neurospheres produced in EGF alone generated 4 times as many glial cells than those produced in EGF plus CNTF. Therefore, neural stem cells differentiate to glial cells by default, which can be inhibited by CNTF.

EPO, on the other hand, reduced the number of neural stem cells by about 50% and increased neurogenesis. Therefore, even though neural stem cells spontaneously differentiate to the glial lineage, a portion of neural stem cells can be induced to form neuronal progenitor cells by EPO. Furthermore, infusion of anti-EPO antibodies, but not nonspecific IgG, led to an increase of neural stem cells, indicating that there is an on-going neurogenesis process in vivo that involves EPO.

EXAMPLE 2

The Effect of Factor Combinations in a Stroke Model

In order to determine the effect of various combinations of factors in animals that suffer a brain injury, focal ischemic injuries were introduced into the brains of rats as a model of stroke. As a result of the brain injury, the animals had lesions in the motor cortex and behaved abnormally in two behavioral tests. One is the forelimb inhibition test, a sensitive measure of functional integrity of regions of the anterior neocortex. Normal rats inhibit the use of forelimbs when they swim, but when one side of the motor cortex was injured in this experiment, the rats failed to inhibit the use of the contralateral forelimb as the motor cortex controls the contralateral side of the body. In the other test, the forelimb asymmetry test, normal rats use both forelimbs equally when they try to balance themselves. The injured animals, however, preferred to use the ipsilateral forelimb, presumably because they could not control their contralateral forelimbs.

The animals then received various test factors, and the effects of these factors on the forelimb inhibition test and brain anatomy were assessed. As controls, a sham control group received a sham brain injury and no test factors, and a vehicle control group received the brain injury as well as infusions of artificial cerebral spinal fluid (CSF). The treatments each test group received are summarized below:

The schedule and procedure of the brain injury, infusion, behavioral test and anatomical analysis are described in Materials and Methods.

A. The Effect of Prolactin and Prolactin Plus EPO

Before the brain injury, all rats inhibited both forepaws in the forelimb inhibition test, which is expected from normal rats. After the injury, all ischemic groups (Groups 2–6) failed to inhibit the contralateral forepaw, but they continued to inhibit the ipsilateral forepaw. Upon infusion of the test factors, the two prolactin groups (Groups 3 and 4) showed greater forepaw inhibition. In fact, by the end of the last week (4 weeks after completion of the infusions), the prolactin plus EPO group (Group 4) was indistinguishable from the controls. Therefore, prolactin, and particularly the combination of prolactin and EPO, resulted in a recovery from a representative symptom of stroke.

Anatomically, the prolactin group showed a high degree of doublecortin staining in the brain, indicating that prolactin induced extensive neurogenesis. The rats in the prolactin plus EPO group had an expanded subventricular zone, indicating a significant cell increase in this area. In addition, many doublecortin positive cells appeared in the legioned area, white matter and the lateral ventricle. A stream of doublecortin positive cells could be observed between the subventricular zone and the lesioned area. Since doublecortin is a marker of migrating neuronal progenitor cells, these results indicate that neural stem cells gave rise to neuronal progenitor cells upon treatment, and the progenitor cells migrated to the lesioned area. The new growth in the lesioned area was so extensive that the cavities created by the ischemic injury were completely or partially filled up in a majority of the rats in this group. These anatomical results thus strongly support the behavioral study that prolactin, or the combination of prolactin and EPO, can be used to treat brain injuries such as stroke.

B. The Effect of Growth Hormone and Growth Hormone Plus EPO

The results of the forelimb asymmetry test indicate that although the extent of asymmetry decreased at the end of week six in all the test groups, the groups receiving growth hormone (Groups 3 and 4) showed a faster and more extensive recovery in the first four weeks. These results are consistent with those from the anatomical analysis, which show that growth hormone alone (Group 3) resulted in increased doublecortin positive cells, and the combination of growth hormone and EPO (Growth 4) led to migration of doublecortin positive cells around the lateral ventricle.

Accordingly, growth hormone, either alone or in conjunction with EPO, improved a motor neuron-related function in a stroke model as well as neuron formation/migration in the brain, indicating that growth hormone can be used to treat or ameliorate brain injuries.

| Group | Brain Injury | First Infusion (days 1–7) | Second Infusion (days 8–14) |
|---|---|---|---|
| 1 | sham | none | none |
| 2 | yes | CSF | CSF |
| 3 | yes | prolactin | CSF |
| 4 | yes | prolactin | erythropoietin (EPO) |
| 5 | yes | growth hormone | CSF |
| 6 | yes | growth hormone | erythropoietin (EPO) |

Thus, prolactin and the combination of prolactin and EPO improved the motor function of injured rats in the forelimb inhibition test but not the forelimb asymmetry test, while growth hormone and its combination with EPO had the reversed effect. These results demonstrate that different factors can stimulate different neural pathways and enhance the recovery of different neuronal circuits, indicating that it is important to combine various factors for a more complete and effective therapeutic result.

We claim:

1. A method for enhancing the formation of neuronal precursor cells or glial precursor cells from neural stem cells in a mammal, comprising administering to the mammal an effective amount of a prolactin to increase the number of neural stem cells in the mammal, and an effective amount of an erythropoietin (EPO) to enhance the formation of neuronal precursor cells or glial cells from neural stem cells.

2. The method of claim 1, wherein the prolactin is administered prior to the EPO.

3. The method of claim 1, wherein the prolactin and the EPO are administered concurrently.

4. The method of claim 1, wherein the neural stem cells are not embryonic cells.

5. The method of claim 1, wherein the neural stem cells are adult neural stem cells.

6. The method of claim 1 wherein the neural stem cells are located in the subventricular zone of the forebrain of the mammal.

7. The method of claim 1 wherein the prolactin and EPO are administered to a ventricle of the brain of the mammal.

8. The method of claim 1 wherein the mammal is suffering from or suspected of having a neurodegenerative disease or condition.

9. The method of claim 8 wherein the disease or condition is brain injury.

10. The method of claim 9 wherein the brain injury is a stroke.

11. The method of claim 8 wherein the disease or condition is selected from the group consisting of Alzheimer's disease, multiple sclerosis (MS), Huntington's disease, amyotrophic lateral sclerosis, and Parkinson's disease.

12. A method for enhancing the formation of neuronal precursor cells from neural stem cells in a mammal, comprising administering to the mammal an effective amount of a prolactin to increase the number of neural stem cells in the mammal, and an effective amount of an erythropoietin (EPO) to enhance the formation of neuronal precursor cells from neural stem cells, wherein the prolactin is administered by subcutaneous administration.

13. The method of claim 12, wherein the prolactin is administered prior to the EPO.

14. The method of claim 12, wherein the prolactin and the EPO are administered concurrently.

15. The method of claim 12, wherein the neural stem cells are not embryonic cells.

16. The method of claim 12, wherein the neural stem cells are adult neural stem cells.

17. The method of claim 12 wherein the neural stem cells are located in the subventricular zone of the forebrain of the mammal.

18. The method of claim 12 wherein the EPO is administered to a ventricle of the brain of the mammal.

19. The method of claim 12 wherein the mammal is suffering from or suspected of having a neurodegenerative disease or condition.

20. The method of claim 19 wherein the disease or condition is brain injury.

21. The method of claim 20 wherein the brain injury is a stroke.

22. The method of claim 19 wherein the disease or condition is selected from the group consisting of Alzheimer's disease, multiple sclerosis (MS), Huntington's disease, amyotrophic lateral sclerosis, and Parkinson's disease.

* * * * *